United States Patent [19]

Owades

[11] Patent Number: 4,765,993

[45] Date of Patent: Aug. 23, 1988

[54] PREPARATION OF ALCOHOL-FREE BARLEY MALT-BASED BEVERAGE

[76] Inventor: Joseph L. Owades, 2164 Hyde St., San Francisco, Calif. 94109

[21] Appl. No.: 4,594

[22] Filed: Jan. 20, 1987

[51] Int. Cl.$^4$ .................. A23L 1/105; A23L 1/186; A23L 2/00

[52] U.S. Cl. .................. 426/29; 426/64; 426/590

[58] Field of Search .................. 426/28, 7, 29, 8, 16, 426/520, 18, 19, 61, 64, 600, 592, 521, 590–591, 392, 397; 435/93–99

[56] References Cited

U.S. PATENT DOCUMENTS

| | | | |
|---|---|---|---|
| 3,679,431 | 7/1972 | Clayton et al. | 426/29 |
| 3,712,820 | 1/1973 | Walmsley et al. | 426/29 |
| 4,138,499 | 2/1979 | Strauss et al. | 426/29 |
| 4,285,975 | 8/1981 | Glenister | 426/29 |
| 4,622,224 | 11/1986 | Owades | 426/29 |

*Primary Examiner*—Marianne Cintins
*Attorney, Agent, or Firm*—Hayes, Davis & Soloway

[57] ABSTRACT

A method for preparing an alcohol-free barley malt-based beverage of reduced caloric content is described. In a preferred embodiment, the method consists of adding to a conventionally procssed Malta beverage, following boiling, cooling and filtering, but prior to packaging an amylolytic enzyme system. The amylolytic enzyme system converts te maltose and complex carbohydrates (dextrins) present in the beverage extract to simple, sweet-tasting dextrose.

6 Claims, No Drawings

PREPARATION OF ALCOHOL-FREE BARLEY MALT-BASED BEVERAGE

FIELD OF THE INVENTION

The present invention relates generally to a method for preparing an alcohol-free barley malt-based beverage and to a beverage so produced. More particularly, the invention relates to a method for preparing a carbonated, alcohol-free barley malt-based beverage of the so-called "Malta" type and characterized by a sweetness and flavor intensity traditionally associated with a conventional Malta beverage, but having a reduced caloric content.

DESCRIPTION OF THE PRIOR ART

Malta is a popular beverage amongst inhabitants of the countries bordering the Carribean Sea, and descendents thereof. Malta comprises a carbonated alcohol-free beverage made from barley malt, corn, molasses or cane sugar, hops and caramel. Malta is a particular popular beverage amongst young people; however, many adults cease drinking Malta due to its high caloric content.

Malta conventionally is made by first mashing a mixture of barley malts with warm water, e.g. at about 50°C., in one vessel, the "mash tub"; boiling cereal adjuncts, e.g. corn grits in water in a second vessel, the "cooker", and then adding the boiling contents of the cooker to the warm malt suspension in the mash tub. This serves to raise the temperature of the mash tub contents to about 65°C. where it is held for about half an hour. The temperature of the combined mash is then raised to about 75°C., and the mash pumped to a straining vessel (a Lauter tub or a mash filter). The action of the amylolytic enzymes naturally present in barley malt converts about 65% of the starch in the malt and corn or other cereals to sweet, simple sugars but leaves about 35% in the form of tasteless complex carbohydrates (dextrins). The clear filtrate is then brought to boiling, a quantity of hops added for flavoring, together with caramel for coloring and a sweetening agent such as corn syrup or cane sugar.

The resulting boiled liquid is then rapidly cooled to about 0°C., carbonated, filtered, packaged, and pasteurized.

Recently, there has developed consumer interest in a Malta of reduced caloric content. Earlier attempts to reduce the caloric content of Malta by diluting it with water have not proved satisfactory, since this results in a Malta of reduced flavor intensity and sweetness.

It is thus a primary object of the present invention to provide a new and improved process for producing a Malta which overcomes the disadvantages of the prior art.

A more specific object of the present invention is to produce a Malta of typical sweetness but reduced caloric content by converting the maltose and the complex carbohydrates (dextrins) normally present in any extract of malt and cereal grains to simple, sweet-tasting dextrose.

This is achieved by adding to a conventionally processed Malta beverage, following boiling, cooling and filtering, but before packaging, an amylolytic enzyme system, typically containing amyloglucosidase, with or without pullulanase, or pullulanase and bacterial α-amylase. These enzymes will hydrolyze the 1,6'-linkage in dextrins still present in the beverage, and produce additional glucose from the debranched molecules. These enzymes also will produce two molecules of glucose from one molecule of maltose, thereby further increasing the sweet sugar (glucose) content of the beverage.

This permits a reduction in the quantity of sugar employed in the basic Malta formulation, or, in the alternative, reduced quantities of the complex carbohydrate yielding materials i.e. corn and barley malt employed in the basic Malta formulation, without loss of flavor or sweetness. This reduction in the quantity of sugar and/or complex carbohydrate yielding materials employed in the basic Malta formulation results in a Malta of lower caloric content than a conventionally produced Malta, and one which is more economical to produce. In a particularly preferred embodiment of the invention the amylolytic enzyme comprises glucoamylase, which is added to the Malta beverage in an amount of from about 0.008 to 0.1 weight percent of the Malta beverage just prior to packaging.

Generally, the process of the present invention employs conventional prior art procedures for the initial process steps. However, unlike prior art Malta preparations the amount of grains and/or corn syrup and sugar employed in the basic Malta formulation may be reduced by 20–35%, and the total solids content reduced from about 12% to about 9%. Thereafter, in accordance with the present invention an amylolytic enzyme system is added to the beverage, the beverage is then carbonated, packaged, and pasteurized. The resulting Malta beverage has the flavor and sweetness of a conventionally prepared Malta, but a reduced caloric content and reduced total solids.

A critical feature and requirement of the instant invention is the addition of the enzyme system to the beverage following boiling but prior to packaging.

Preferably the enzyme system comprises a glucoamylase whereby essentially every glucosidic bond contained in the maltose and in the complex-carbohydrates still present in the Malta will be converted to simple, sweet sugars, i.e. d-glucose. This additional sweetness permits the production of a final Malta beverage product using less materials and containing fewer calories per fluid ounce.

The enzyme system should be one which is functional at or above the pasteurizing temperature employed in the production of Malta, typically about 140° F. A number of commercially available enzymes are available which meet the aforesaid criteria, amongst which are mentioned Adjuzyme available from Enzyme Development Corp. and Dextrazyme, available from NOVO Industries; and may be added prior to, concurrently with or following carbonation. Of course, the enzyme system must be added prior to packaging.

The present invention will be further described in the following working examples:

WORKING EXAMPLES

Example I comprises the traditional production of Malta. Examples II and III illustrate this invention.

In each example 100 barrels of finished Malta beverage product is produced.

EXAMPLE I (Prior Art)

80 pounds of malt and 860 pounds of corn grits were added to 10 barrels of water, and the resulting mixture heated to boiling, with stirring, for 30 minutes in a cereal cooker.

Concurrently, 1400 pounds of ground barley malt and 867 pounds of caramel malt were added to 20 barrels of water, and heated to about 50°C., with stirring, in a mash tub. The resulting malt mash was held at 50°C. for ten minutes, and the contents of the cereal cooker were then rapidly pumped over into the mash tub, and stirred. The temperature of the resulting mixture at the completion of the addition of the malt mash was about 65°C.. The combined mash was held at about 65°C. for 30 minutes, and then the temperature of the combined mash was raised to 75°C., and the mash pumped to a Lauter tub and sparged with hot water.

The resulting clear liquid was then heated to boiling, 2 pounds of hops added for flavoring, 1,067 pounds of cane sugar added for sweetness, and ten gallons of caramel added for coloring.

The resulting boiled liquid was then rapidly cooled to about 0°C., and the finished product, 100 barrels, was carbonated, filtered and packaged.

The resulting beverage had the usual sweet malt flavor and visual appearance of Malta beverage product.

EXAMPLE II

The procedure of Example I was repeated, but employing the following combination of materials: 1,110 pounds of barley malt, 650 pounds of caramel malt, 650 pounds of corn grits, 800 pounds cane sugar, 10 gallons of caramel and 2 pounds of hops. Processing was identical except three liters (7 pounds) of glucoamylase available from Enzyme Development Corp. under the name Adjuzyme was added to the liquid following carbonation and filtering, and just prior to packaging. As before, 100 barrels of beverage product were produced.

EXAMPLE III

The procedure of Example II was repeated, but using the following materials: 1,480 pounds of barley malt, 867 pounds of caramel malt, 860 pounds of corn grits, 500 pounds of high fructose corn syrup, 10 gallons of caramel, 2 pounds of hops and 3.5 liters (8 pounds) of Adjuzyme brand glucoamylase available from Enzyme Development Corp. As in the case of Example II the glucoamylase was added to the Ma[ta product following carbonation and filtration, but prior to packaging. 100 bbls. of finished product was produced.

The products from Examples II and III were equally sweet tasting to that from Example I.

As appears clearly from the foregoing, adding a small quantity of an amylolytic enzyme system to a Malta beverage just prior to packaging permits the production of a Malta beverage of conventional flavor intensity, aroma, color and sweetness, but having reduced caloric content.

The process appears to be independent of the amount of amylolytic enzyme added since the amylolytic enzyme acts only as a catalyst and is otherwise unchanged. However, the speed of conversion of the glycosidic bonds of the complex carbohydrates contained in the beverage product to d-glucose has been observed to be dependent somewhat on the concentration of the amylolytic enzyme system. Generally, for producing 100 barrels of Malta, from 0.008 to 0.1 parts by weight of enzymes should be added in order to effect essentially complete conversion of the glucosidic bonds to d-glucose within seven to ten days after packaging which typically is adequate for most commercial purposes since the Malta typically will be in shipment and storage at least for that period of time. With the addition of 0.008 to 0.1 parts by weight of amylolytic enzyme to 100 barrels of Malta, essentially 100 percent of the glucosidic bonds initially present in the beverage product will be converted to d-glucose within about seven days of the addition. The addition of more than about 0.1 parts by weight of amylolytic enzyme system per 100 barrels of Malta generally is not necessary, and adds to manufacturing costs.

As it appears clearly from the foregoing, adding a small quantity of an amylolytic enzyme system to a freshly "brewed" Malta beverage product produces a novel Malta beverage product of flavor, aroma and sweetness resembling conventionally prepared Malta beverage but characterized by reduced caloric content.

Since certain changes may be made in the above process and products without departing from the scope of the invention herein involved, it is intended that all matter contained in the above description shall be interpreted in an illustrative and not in a limiting sense.

I claim:

1. In a method for producing an alcohol-free beverage in which a warm malt mash and boiling cereal adjuncts are sequentially blended, boiled, cooled, carbonated, filtered, packaged and pasteurized, the improvement which comprises adding to the resulting beverage after filtering and prior to packaging an enzyme system comprising one or a mixture of amylolytic enzymes in a sufficient amount and for a sufficient period of time to convert maltose and complex carbohydrates present in the resulting product to dextrose.

2. In a method according to claim 1, the improvement wherein said amylolytic enzymes are selected from the group consisting of glucoamylase, pullulanase, bacterial α-amylase, and mixtures thereof.

3. In a method according to claim 1, the improvement wherein said amylolytic enzymes are added to said beverage in an amount of from about 0.008 to 0.10 percent of the beverage.

4. A method of producing an alcohol-free barley malt based beverage of reduced caloric content comprising the sequential steps of:
  (a) forming a warm suspension of barley malt in water;
  (b) forming a boiling suspension of cereal adjunct in water;
  (c) blending said warm suspension of barley malt and said boiling suspension of cereal adjuncts;
  (d) sequentially boiling, cooling, carbonating and filtering the resulting blend from step (c);
  (e) adding one or a mixture of amylolytic enzymes to the resulting filtered product from step (d) in a sufficient amount and for a suffient period of time to convert maltose and complex carbohydrates present in the resulting product to dextrose; and
  (f) packaging and pasteurizing the resulting product from step (e).

5. A method according to claim 4, wherein said amylolytic enzymes are selected from the group consisting of glucoamylase, pullulanase, bacterial α-amylase and mixtures thereof.

6. A method according to claim 4, wherein said amylolytic enzymes are added in an amount of from about 0.008 to about 0.1 weight percent of the beverage product.

* * * * *